United States Patent
Mistretta et al.

(10) Patent No.: US 8,654,119 B2
(45) Date of Patent: *Feb. 18, 2014

(54) SYSTEM AND METHOD FOR FOUR DIMENSIONAL ANGIOGRAPHY AND FLUOROSCOPY

(75) Inventors: Charles A. Mistretta, Madison, WI (US); Charles M. Strother, Madison, WI (US)

(73) Assignees: Mistretta Medical, LLC, Madison, WI (US); CMS Medical, LLC, Madison, WI (US)

( * ) Notice: Subject to any disclaimer, the term of this patent is extended or adjusted under 35 U.S.C. 154(b) by 494 days.
This patent is subject to a terminal disclaimer.

(21) Appl. No.: 12/692,340

(22) Filed: Jan. 22, 2010

(65) Prior Publication Data
US 2011/0038517 A1 Feb. 17, 2011

Related U.S. Application Data

(63) Continuation-in-part of application No. 12/542,376, filed on Aug. 17, 2009.

(51) Int. Cl.
*G06T 15/00* (2011.01)
*A61B 6/00* (2006.01)
*H05G 1/60* (2006.01)

(52) U.S. Cl.
USPC .................. 345/419; 378/4; 378/901; 378/9

(58) Field of Classification Search
None
See application file for complete search history.

(56) References Cited

U.S. PATENT DOCUMENTS 4,482,918 A 11/1984 Keyes et al.
6,317,621 B1 11/2001 Graumann et al.
(Continued)

FOREIGN PATENT DOCUMENTS

WO WO-2006/106470 10/2006

OTHER PUBLICATIONS

Holger Schmitt, Michael Grass, Rolf Suurmond, Thomas Köhler, Volker Rasche, Stefan Hähnel, Sabine Heiland, Reconstruction of blood propagation in three-dimensional rotational X-ray angiography (3D-RA), Computerized Medical Imaging and Graphics, vol. 29, Issue 7, Oct. 2005, pp. 507-520.*

(Continued)

*Primary Examiner* — Kee M Tung
*Assistant Examiner* — Zhengxi Liu
(74) *Attorney, Agent, or Firm* — Foley & Lardner LLP

(57) ABSTRACT

A method for generating time-resolved 3D medical images of a subject by imparting temporal information from a time-series of 2D medical images into 3D images of the subject. Generally speaking, this is achieved by acquiring image data using a medical imaging system, generating a time-series of 2D images of a ROI from at least a portion of the acquired image data, reconstructing a 3D image substantially without temporal resolution from the acquired image data, and selectively combining the time series of 2D images with the 3D image. Selective combination typically involves registering frames of the time-series of 2D images with the 3D image, projecting pixel values from the 2D image frames "into" the 3D image, and weighting the 3D image with the projected pixel values for each frame of the time-series of 2D images. This method is particularly useful for generating 4D-DSA images (that is, time-resolved 3D-DSA images) from a time-series of 2D-DSA images acquired via single plane or biplane x-ray acquisitions with 3D images acquired via a rotational DSA acquisition. 4D-DSA images can be generated either by using multiple injections or by using a single injection by combining a time-series of 2D-DSA images generated from individual projections from a rotational x-ray acquisition with a 3D image reconstructed from substantially all of the projection views acquired during the rotational x-ray acquisition. These DSA images may have a spatial resolution on the order of $512^3$ pixels and a temporal resolution of about 30 frames per second, which represents an increase over traditional 3D-DSA frame rates by a factor of between 150 and 600.

31 Claims, 13 Drawing Sheets

(56) References Cited

U.S. PATENT DOCUMENTS

| | | | |
|---|---|---|---|
| 6,823,204 | B2 | 11/2004 | Grass et al. |
| 6,983,182 | B2 | 1/2006 | Mistretta |
| 7,305,062 | B2 | 12/2007 | Hambuchen et al. |
| 7,545,901 | B2 | 6/2009 | Mistretta |
| 7,590,442 | B2 | 9/2009 | Boese et al. |
| 7,738,626 | B2 * | 6/2010 | Weese et al. ............ 378/41 |
| 8,009,885 | B2 * | 8/2011 | Grass et al. ............ 382/128 |
| 2001/0007593 | A1 | 7/2001 | Oosawa |
| 2004/0116812 | A1 * | 6/2004 | Selzer et al. ............ 600/467 |
| 2005/0080328 | A1 * | 4/2005 | Vass et al. ............ 600/407 |
| 2005/0084060 | A1 | 4/2005 | Seppi et al. |
| 2005/0232389 | A1 | 10/2005 | Klingenbeck-Regn |
| 2006/0165213 | A1 | 7/2006 | Hambuchen et al. |
| 2006/0173297 | A1 | 8/2006 | Popescu |
| 2006/0250386 | A1 | 11/2006 | Movassaghi et al. |
| 2007/0009080 | A1 * | 1/2007 | Mistretta ............ 378/4 |
| 2007/0055148 | A1 | 3/2007 | Klingenbeck-Regn |
| 2007/0183569 | A1 | 8/2007 | Boese et al. |
| 2008/0051648 | A1 | 2/2008 | Suri et al. |
| 2008/0192997 | A1 | 8/2008 | Grass et al. |
| 2008/0212857 | A1 | 9/2008 | Pfister et al. |
| 2008/0243435 | A1 | 10/2008 | Deinzer et al. |
| 2008/0300478 | A1 | 12/2008 | Zuhars et al. |
| 2009/0010380 | A1 | 1/2009 | Gotoh |
| 2009/0074277 | A1 | 3/2009 | Deinzer et al. |
| 2009/0088830 | A1 | 4/2009 | Mohamed et al. |
| 2009/0093712 | A1 | 4/2009 | Busch et al. |
| 2010/0053209 | A1 * | 3/2010 | Rauch et al. ............ 345/619 |
| 2010/0061611 | A1 * | 3/2010 | Xu et al. ............ 382/131 |
| 2010/0201786 | A1 * | 8/2010 | Schaefer et al. ............ 348/47 |
| 2010/0296623 | A1 * | 11/2010 | Mielekamp et al. ............ 378/4 |
| 2011/0038517 | A1 | 2/2011 | Mistretta et al. |

OTHER PUBLICATIONS

Mistretta et al, "HYPR: Constrained reconstruction for enhanced SNR in dynamic medical imaging" Medical Imaging 2008: Physics of Medical Imaging. Edited by Hsieh, Jiang; Samei, Ehsan. Proceedings of the SPIE, vol. 6913, pp. 691305-691305-9 (2008).*

Kohler, T.; Schmitt, H.; Heiland, S.; Grass, M.; , "Method for flow reconstruction from dynamic X-ray projection measurements," Nuclear Science Symposium Conference Record, 2004 IEEE , vol. 5, no., pp. 3295-3298 vol. 5, Oct. 16-22, 2004.*

Zikuan Chen, Ruola Ning, David Conover and Xianghua Lu, "Blood flow measurement by cone-beam CT bolus imaging", Proc. SPIE 6143, 61432J (2006).*

Schmitt, H.; Grass, M.; Rasche, V.; Schramm, O.; Haehnel, S.; Sartor, K.; , "An X-ray-based method for the determination of the contrast agent propagation in 3-D vessel structures," Medical Imaging, IEEE Transactions on , vol. 21, No. 3, pp. 251-262, Mar. 2002.*

"nth Root" http://www.mathsisfun.com/numbers/nth-root.html. Archived on Dec. 21, 2007. Retrieved on Jul. 10, 2012 from <http://web.archive.org/web/20071221121146/http://www.mathsisfun.com/numbers/nth-root.html>.*

Waechter I, Bredno J, Weese J, Barratt DC, Hawkes DJ. Using flow information to support 3D vessel reconstruction from rotational angiography. Med Phys 2008;37:3302-3316.*

Liu X, Primak AN, Krier JD, Yu L, Lerman LO, et al. (Oct. 2009) Renal perfusion and hemodynamics: accurate in vivo determination at CT with a 10-fold decrease in radiation dose and HYPR noise reduction. Radiology 253: 98-105.*

International Search Report and Written Opinion for International Application No. PCT/US2010/045637, mail date Apr. 12, 2011, 7 pages.

Lessard, S. et al., "Automatically driven vector for line segmentation in 2D and biplane imaging modality," 15 International Conference of Image Analysis and Processing, Italy, Sep. 8-11, 2009 (9 pages).

Pollmann, S.I. et al., "Four dimensional intravenous cone-beam computed tomographic subtraction angiography," Invest. Radiol. (2008) 43(11):753-761.

Schmitt, H. et al., "Reconstruction of blood propagation in three-dimensional rotational X-ray angiography (3D-RA)," Comp. Med. Imag. Graph. (2005) 29:507-520.

International Search Report and Written Opinion for PCT Application No. PCT/US2011/022120, mail date Aug. 26, 2011, 9 pages.

International Search Report and Written Opinion for PCT Application No. PCT/US2012/042491, mailed Mar. 4, 2013, 10 pages.

* cited by examiner

SYSTEM AND METHOD FOR FOUR DIMENSIONAL ANGIOGRAPHY AND FLUOROSCOPY

CROSS-REFERENCE TO RELATED APPLICATIONS

This application is a continuation-in-part of U.S. patent application Ser. No. 12/542,376 titled SYSTEM AND METHOD OF TIME-RESOLVED, THREE-DIMENSIONAL ANGIOGRAPHY filed Aug. 17, 2009, which is hereby incorporated by reference in its entirety herein.

BACKGROUND OF THE INVENTION

The present invention relates to angiography and, more particularly, to a system and method for producing time-resolved, three-dimensional (thus, resulting in four dimensional) angiographic and fluoroscopic images.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. For decades, post-processing of images was largely limited to the use of film subtraction techniques. Initial angiographic techniques involved direct arterial punctures and the manipulation of a needle through which a contrast medium was injected. These practices were associated with a significant incidence of serious complications. The development of percutaneous techniques allowing the use of a single catheter to study multiple arterial segments reduced, but this by no means eliminated, these adverse events. In the late 1970's, a technique known as digital subtraction angiography (hereinafter, "DSA") was developed based on real-time digital processing equipment. Because of the advantages of digital processing, it was originally hoped that DSA could be consistently implemented using an intravenous (hereinafter, "IV") injection of contrast medium, thus reducing both the discomfort and the incidence of complications associated with direct intraarterial (hereinafter, "IA") injections.

However, it quickly became apparent that the IV-DSA technique was limited by problems due to suboptimal viewing angles and vessel overlap that could only be reduced by repeated injections. Even then, these factors were problematic unless a projection that avoided the overlap of relevant vascular structures could be defined. Similar problems occurred when using biplane acquisitions. Also, because of the limited amount of signal associated with the IV injection of contrast medium, IV-DSA was best performed in conditions with adequate cardiac output and minimal patient motion. IV-DSA was consequently replaced by techniques that combined similar digital processing with standard IA angiographic examinations. Nevertheless, because DSA can significantly reduce both the time necessary to perform an angiographic examination and the amount of contrast medium that was required, its availability resulted in a significant reduction in the adverse events associated with angiography. Due to steady advancements in both hardware and software, DSA can now provide exquisite depictions of the vasculature in both two-dimensional (hereinafter, "2D") and rotational three-dimensional (hereinafter, "3D") formats. 3D-DSA has become an important component in the diagnosis and management of people with a large variety of central nervous system vascular diseases.

Current limitations in the temporal resolution capabilities of x-ray angiographic equipment require that rotational acquisitions be obtained over a minimum time of about 5 seconds. Even with perfect timing of an acquisition so that arterial structures are fully opacified at the onset of a rotation, there is almost always some filling of venous structures by the end of the rotation. Display of a "pure" image of arterial anatomy is only achieved by thresholding such that venous structures, which contain lower concentrations of contrast medium than arterial structures, are no longer apparent in the image. This limitation is a significant factor in making it prohibitively difficult to accurately measure the dimensions of both normal and abnormal vascular structures. Current DSA-based techniques do not depict the temporal sequence of filling in a reconstructed 3D-DSA volume.

In recent years competition for traditional DSA has emerged in the form of computed tomography angiography (hereinafter, "CTA") and Magnetic Resonance Angiography (hereinafter, "MRA"). CTA provides high spatial resolution, but it is not time-resolved unless the imaging volume is severely limited. CTA is also limited as a standalone diagnostic modality by artifacts caused by bone at the skull base and the contamination of arterial images with opacified venous structures. Further, CTA provides no functionality for guiding or monitoring minimally-invasive endovascular interventions. Significant advances have been made in both the spatial and the temporal resolution qualities of MRA. Currently, gadolinium-enhanced time-resolved MRA (hereinafter, "TRICKS") is widely viewed as a dominant clinical standard for time-resolved MRA. TRICKS enables voxel sizes of about 10 mm$^3$ and a temporal resolution of approximately 10 seconds. Advancements such as HYBRID HYPR MRA techniques, which violate the Nyquist theorem by factors approaching 1000, can provide images with sub-millimeter isotropic resolution at frame times just under 1 second. Nonetheless, the spatial and temporal resolution of MRA are not adequate for all imaging situations and its costs are considerable.

Shortcomings of existing angiography methods are particularly prevalent when imaging the small size and convoluted course of the intracranial vasculature. With traditional DSA it is difficult or impossible to image and display these structures without the overlap of adjacent vessels. This problem is compounded when visualizing abnormal structures with complex geometry, such as aneurysms, or when abnormally fast or slow flow is present, such as in vascular malformations or ischemic strokes. As cerebrovascular diseases are increasingly treated using minimally invasive endovascular techniques, where such treatment is dependent upon imaging techniques for visualization of vascular structures, it is becoming more important to develop imaging methods that allow clear definition of vascular anatomy and flow patterns. Such information is becoming a prerequisite for both pretreatment planning and the guidance of interventional procedures. For example, the endovascular treatment of vascular disease can require accurate navigation through the small and tortuous vessels of the brain and spinal cord. Currently this involves the use of a roadmap that must be "reset" numerous times during a typical procedure. In fact, it is not uncommon to have 15 to 20 resets during a given procedure. Not only does this use large amounts of contrast medium, but the risk of thromboembolic complications increases with each injection.

It would therefore be desirable to have a system and method for producing time-resolved, 3D images of the vasculature with an improved spatial and temporal resolution over those possible currently. The method would allow arterial vasculature to be distinguished from venous vasculature, which would in turn allow the use of IV injections of contrast medium in cases where IA injections are currently performed.

This would also allow 3D volumes to be viewed as a dynamic sequence, allowing an improved understanding of vascular diseases and providing a basis for more accurate and versatile roadmaps for use in interventional procedures.

BRIEF SUMMARY OF THE INVENTION

The present invention overcomes the aforementioned drawbacks by providing a system and method for generating a detailed series of time-resolved, 3D medical images of a subject, with both high temporal resolution and excellent spatial resolution, by imparting temporal information from either a separately acquired time-series of 2D images into a still 3D rotational DSA image or, in a preferred embodiment, using the intrinsic time information provided by the 2D projection images from which the 3D rotational DSA image is formed. In the preferred method, image data from a subject is acquired using a medical imaging system and a single contrast injection to generate a time-series of 2D images from which a 3D image, substantially without temporal resolution, is reconstructed from at least a portion of the acquired image data consisting of 2D angular projections. The method also includes producing a series of time-resolved 3D images of the subject by selectively combining the 3D image, substantially without temporal resolution, and the time-series of 2D images. This preferred method can be implemented with a system consisting of a single x-ray source and detector array. In the preferred method, the signal-to-noise ratio of each image in the time series is substantially the same as that of the single 3D image. In the preferred method, it has been discovered that pairs of projections can be separated by angles on the order of 60 degrees. In spite of this, the temporal behavior is dominated by the earlier projection whereas the second serves primarily to remove potential ambiguities that may occur in the multiplication process. Venous signals in the projection at the larger angle are zeroed since they are not present in the earlier frame. The overall time frame is generally formed as the square root of two products—the product of the first frame projection and the 3D volume, and the product of the second projection and the 3D volume.

In an embodiment of the present invention, a method is provided for producing a time-resolved 3D image of a subject by acquiring time-resolved image data from a region-of-interest (hereinafter, "ROI") in the subject in a first acquisition, performed over a time period during which a bolus of contrast agent passes through the ROI, and then generating a time-series of 2D images from image data acquired in the first acquisition. The method also includes acquiring image data from the ROI in a second acquisition, reconstructing a 3D image substantially without temporal resolution from the image data acquired in the second acquisition, and producing a time-resolved 3D image of the subject by selectively combing the time-series of 2D images and the 3D image substantially without temporal resolution. In this method, the first acquisition may be performed using either a single plane or biplane x-ray system. Once again, the method includes transferring the signal-to-noise ratio of the single 3D image to the individual time frames. This is accomplished through convolution of the projection data prior to multiplication by the 3D volume.

In another embodiment of the present invention, a method is provided for producing a time-resolved 3D image of a subject by acquiring projection views of a region-of-interest (ROI) in the subject over a selected time period using a rotational acquisition, while a bolus of contrast agent passes through the ROI during a portion of the selected time period. Again, the method includes generating a time-series of 2D images of the ROI from projection views acquired during the portion of the selected time period during which the bolus of contrast agent passes through the ROI. This method also includes the reconstruction of a 3D image of the ROI, substantially without temporal resolution, from substantially all of the acquired projection views and producing the time-resolved 3D image of the subject by selectively combining the time-series of 2D images and the 3D image without temporal resolution.

The described method further includes 3D time-resolved tracking on IV devices such as catheters and coils. This process involves the use of a subtracted series of 2D projection images of the device obtained in one or, preferably, two simultaneous projections and the imbedding of this information into a 3D rotational data set so that the position of the device can be displayed from arbitrary angles without rotation of the source or detector system(s). In a preferred implementation, the various segments of the advancing device are processed from time derivative information from two simultaneous projection views. This information is multiplicatively correlated so that at any point in time the current position of the leading edge of the device is identified and can be distinguished from its previous positions. This is important in instances in which there might be coiling of a device whereby it may occupy multiple positions within the vessel lumen. The preferred method includes generating an historical path of the device which sums all previous instantaneous signals identified by the multiplicative correlation process. For application in systems having only a single source/single detector system, advancing devices not resulting in multiple instances within the lumen can be depicted using single view, time-dependent projections and displaying the device along the center line of the vessel in the orthogonal view.

Yet another embodiment of the present invention includes a partial filtered back projection reconstruction employing one or more segments of angles which provide a weighting image that is multiplied into the static 3D rotational vascular data set. This provides a better approximation to the time-dependent perfusion of the intravascular tissue. For single source/single detector systems, the filtered back projection is generated with a single angular segment composed of several adjacent projections. For bi-plane systems, two segments separated by approximately 90 degrees can be employed. To remove the effects of time-dependent vascular behavior, vessels can be segmented out before multiplication of the tissue component of the projections and the tissue component of the static 3D data set.

Additional features and advantages of the present invention are described in, and will be apparent from, the following Detailed Description of the Invention and the Drawing.

DETAILED DESCRIPTION OF THE INVENTION

Figure 1A:
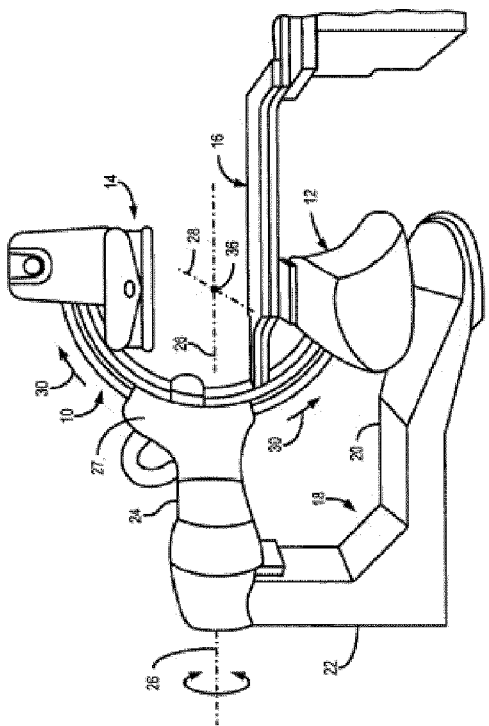
FIGS. 1A and 1B depict a rotational x-ray system configured to carry out a process in accordance with the present invention.

Referring to FIG. 1A, the present invention may employ a rotational x-ray system that is designed specifically for use in connection with interventional procedures. It is characterized by a gantry having a C-arm 10 which carries an x-ray source assembly 12 on one of its ends and an x-ray detector array assembly 14 at its other end. The gantry enables the x-ray source 12 and detector 14 to be oriented in different positions and angles around a patient disposed on a table 16, while enabling a physician access to the patient.

The gantry includes an L-shaped pedestal 18 which has a horizontal leg 20 that extends beneath the table 16 and a vertical leg 22 that extends upward at the end of the horizontal leg 20 that is spaced from of the table 16. A support arm 24 is rotatably fastened to the upper end of vertical leg 22 for rotation about a horizontal pivot axis 26.

The pivot axis 26 is aligned with the centerline of the table 16, and the arm 24 extends radially outward from the pivot axis 26 to support a C-arm drive assembly 27 on its outer end. The C-arm 10 is slidably fastened to the drive assembly 27 and is coupled to a drive motor (not shown) which slides the C-arm 10 to revolve it about a C-axis 28 as indicated by arrows 30. The pivot axis 26 and C-axis 28 intersect each other, at an isocenter 36 located above the table 16, and are perpendicular to each other.

The x-ray source assembly 12 is mounted to one end of the C-arm 10 and the detector array assembly 14 is mounted to its other end. The x-ray source 12 emits a beam of x-rays which are directed at the detector array 14. Both assemblies 12 and 14 extend radially inward to the pivot axis 26 such that the center ray of this beam passes through the system isocenter 36. The center ray of the beam thus can be rotated about the system isocenter around either the pivot axis 26 or the C-axis 28, or both, during the acquisition of x-ray attenuation data from a subject placed on the table 16.

The x-ray source assembly 12 contains an x-ray source which emits a beam of x-rays when energized. The center ray passes through the system isocenter 36 and impinges on a two-dimensional flat panel digital detector housed in the detector assembly 14. The detector 38 is a 2048 by 2048 element two-dimensional array of detector elements having a size of 41 cm by 41 cm. Each element produces an electrical signal that represents the intensity of an impinging x-ray and hence the attenuation of the x-ray as it passes through the patient. During a scan, the x-ray source assembly 12 and detector array assembly 14 are rotated about the system isocenter 36 to acquire x-ray attenuation projection data from different angles. The detector array is able to acquire 30 projections, or views, per second which is the limiting factor that determines how many views can be acquired for a prescribed scan path and speed.

Figure 1B:
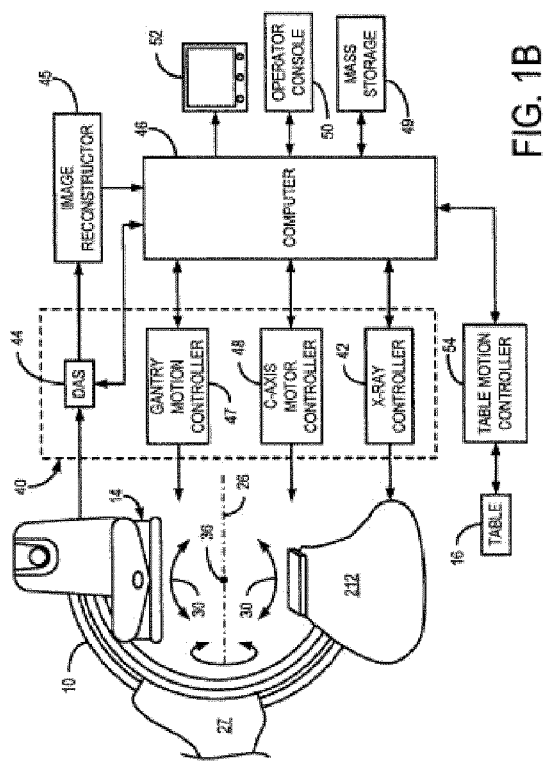

Referring to FIG. 1B, the rotation of the assemblies 12 and 14 and the operation of the x-ray source are governed by a control mechanism 40 of the x-ray system. The control mechanism 40 includes an x-ray controller 42 that provides power and timing signals to the x-ray source 32. A data acquisition system (DAS) 44 in the control mechanism 40 samples data from detector elements 38 and passes the data to an image reconstructor 45. The image reconstructor 45 receives digitized x-ray data from the DAS 44 and performs high speed image reconstruction according to the methods of the present invention. The reconstructed image is applied as an input to a computer 46 which stores the image in a mass storage device 49 or processes the image further to produce parametric images according to the teachings of the present invention. It is contemplated that the computer 46 may be, or include components of, a digital vascular image processor (DVIP) system.

The control mechanism 40 also includes gantry motor controller 47 and a C-axis motor controller 48. In response to motion commands from the computer 46, the motor controllers 47 and 48 provide power to motors in the x-ray system that produce the rotations about respective pivot axis 26 and C-axis 28. As will be discussed below, a program executed by the computer 46 generates motion commands to the motor drives 47 and 48 to move the assemblies 12 and 14 in a prescribed scan path.

The computer 46 also receives commands and scanning parameters from an operator via console 50 that has a keyboard and other manually operable controls. An associated cathode ray tube display 52 allows the operator to observe the reconstructed image and other data from the computer 46. The operator supplied commands are used by the computer 46 under the direction of stored programs to provide control signals and information to the DAS 44, the x-ray controller 42 and the motor controllers 47 and 48. In addition, computer 46 operates a table motor controller 54 which controls the motorized table 16 to position the patient with respect to the system isocenter 36.

Whereas conventional reconstruction methods generally necessitate the acquisition of a minimum number of projections dictated by the Nyquist theorem, the present invention provides a fundamentally new method for imparting temporal resolution from a time-series of 2D images into 3D image volumes to create time-resolved 3D medical images. This allows, among other things, the production of 3D angiograms with both exquisite detail and high temporal resolution. The method can be implemented using a wide-variety of medical imaging systems, such as CT systems, fluoroscopy systems, and the above-discussed rotational x-ray system, either alone or in combination. Accordingly, the present description first presents a generalized method for producing time-resolved 3D images before proceeding to more specific implementations and extensions of the method.

Figure 2:
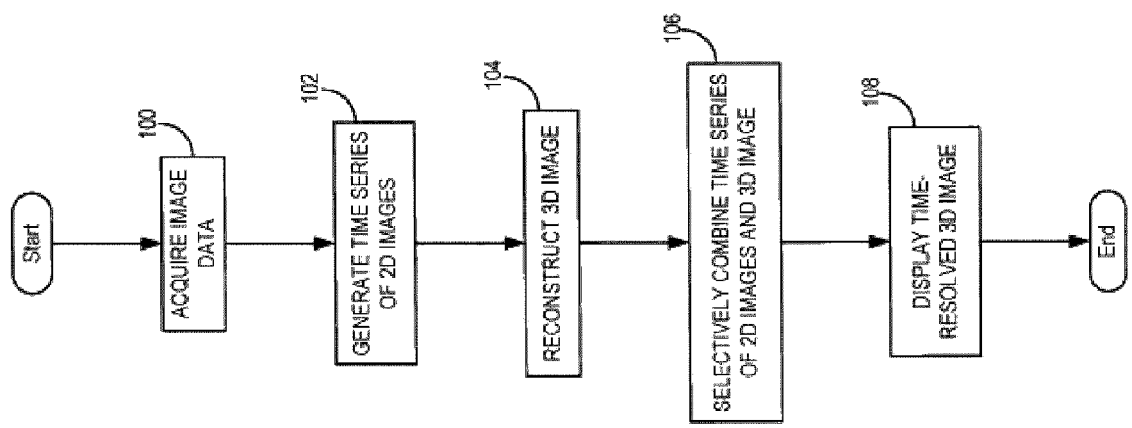
FIG. 2 is a flowchart setting forth the general steps for producing a time-resolved 3D image in accordance with the present invention.

Referring now to FIG. 2, a general method for producing a time-resolved 3D image begins at process block 100 with the acquisition of image data from a region-of-interest (ROI) in a subject using a medical imaging system, such as a CT system or a single-plane, biplane, or rotational x-ray systems. At process block 102, a time-series of 2D images is generated from at least a portion of the acquired image data. While the time-series of 2D images can have a high temporal and spatial resolution and may include images acquired at different angles around the subject, they generally cannot provide a sophisticated 3D depiction of the subject. The production of the time-series of 2D images may be convolved with a convolution kernel in order to provide local spatial coverage with a desired weighting. For example, these weighted images can provide information detailing how much of a vessel tree is present at a given time. It is contemplated that this process can increase SNR by a factor of three over that provided by the original time series pixels when using a 3×3 convolution kernel. At process block 104, a 3D image of the subject is reconstructed from the acquired image data. Though individual projections used to reconstruct this 3D image may themselves convey some degree of temporal information, the reconstructed 3D image itself is substantially free of temporal resolution. For brevity, the 3D image, substantially without temporal resolution, and the time-series of 2D images may simply be referred to as the "3D image" and "2D images," respectively. It should be noted that the acquisition and reconstruction of the above sets of image data can be performed in accordance with constrained reconstruction techniques, such as highly constrained backprojection reconstruction (HYPR), to improve SNR and permit potential radiation and contrast agent dose reductions.

At process block 106, the time-series of 2D images and the static 3D image are selectively combined so that the temporal information included in the 2D images is imparted into the 3D image. This results in the production of a time-resolved 3D image of the subject with high temporal and spatial resolution. While the selective combination process varies based on the medical imaging system used and the nature of the acquired image data, it generally involves the steps of (1) registering the 2D images to the 3D image, (2) projecting the attenuation value of the pixels in the 2D images into the 3D image, and (3) weighting the 3D image with the projected values for each individual frame of the time-series of 2D images. It is contemplated that the temporal weighting in step (3) generally involves multiplying the projected pixel values with the 3D image. These three steps, which can be referred to as "multiplicative projection processing" (MPP), may be accompanied by additional steps to improve image quality or reduce the prevalence of errors and artifacts. For example, the intensity values of pixels and voxels in the 2D images and 3D image produced at process blocks 102 and 104 may quantify an x-ray attenuation level at a given location in the subject. These attenuation levels may not be preserved when multiplying the 3D image with projected pixel values. Accordingly, more accurate indications of the attenuation levels may be restored by taking a root of the intensity value at each voxel in the time-resolved 3D image; for example, by taking the n-th root if (n−1) different sets of 2D images are used to weight the 3D image. Other processing steps can be performed before the time-resolved 3D image is displayed at process block 108.

The 2D images and 3D image produced at process blocks 102 and 104, respectively, can be produced using DSA techniques. That is, 2D images depicting the subject's vasculature can be produced by reconstructing image data acquired as a bolus of contrast passes through the ROI and subtracting out a pre-contrast, or "mask," image acquired before the administration of contrast agent. Likewise, a 3D image of the same vasculature can be produced by reconstructing image data acquired as contrast agent occupies the ROI and subtracting out a mask image to remove signals associated with non-vascular structures. As will be discussed below, depending on the imaging situation, the time series of 2D-DSA images and the 3D-DSA images can be produced from image data acquired using a single medical imaging system and contrast agent injection or from different sets of image data acquired separately using different medical imaging systems and contrast agent injections. In either case, the time-resolved 3D image produced by combining the DSA images depicts the subject's vasculature with both excellent spatial and excellent temporal resolution and thus may be referred to as a 4D-DSA image. In addition, the 4D-DSA images can be displayed as "pure" arterial, pure venous, or composite arterial and venous images and can be fully rotated during each state of the filling of the vasculature, thereby enabling greatly simplified interpretation of vascular dynamics. The spatial resolution of these 4D-DSA images is generally on the order of $512^3$ pixels at about 30 frames per second. This represents an increase over traditional 3D-DSA frame rates by a factor of between 150 and 600, without any significant image quality penalty being incurred.

The acquisition of contrast enhanced image data can be performed following the administration of contrast agent to the subject via either IV or IA injection. When scanning a local area, IA injections allow high image quality and temporal resolution as well as reduced contrast agent dose. However, IV injections are often more suitable for scanning larger regions where multiple IA injections at different locations and different arteries would otherwise be required. For example, there are many clinical cases where multiple 3D-DSA acquisitions, each using a different IA injection, are performed to produce separate studies that can be merged into a larger high quality vascular tree. While separate IA acquisitions may be employed for generating the time-series of 2D images used by the present invention for temporal weighting, the use of an IV injection for this purpose provides a mechanism for simultaneously synchronizing imparting temporal information to all of the previously acquired anatomical locations present in instances when there are multiple, separate, IA 3D-DSA studies. This process reduces the likelihood of complications associated with IA contrast agent injections and improves scan efficiency. Further, there is the filling of arteries and veins with the same concentration of contrast medium in scans performed using IV rather than IA contrast agent injections, thus allowing the visualization of venous and arterial structures at the same threshold.

Figure 3:
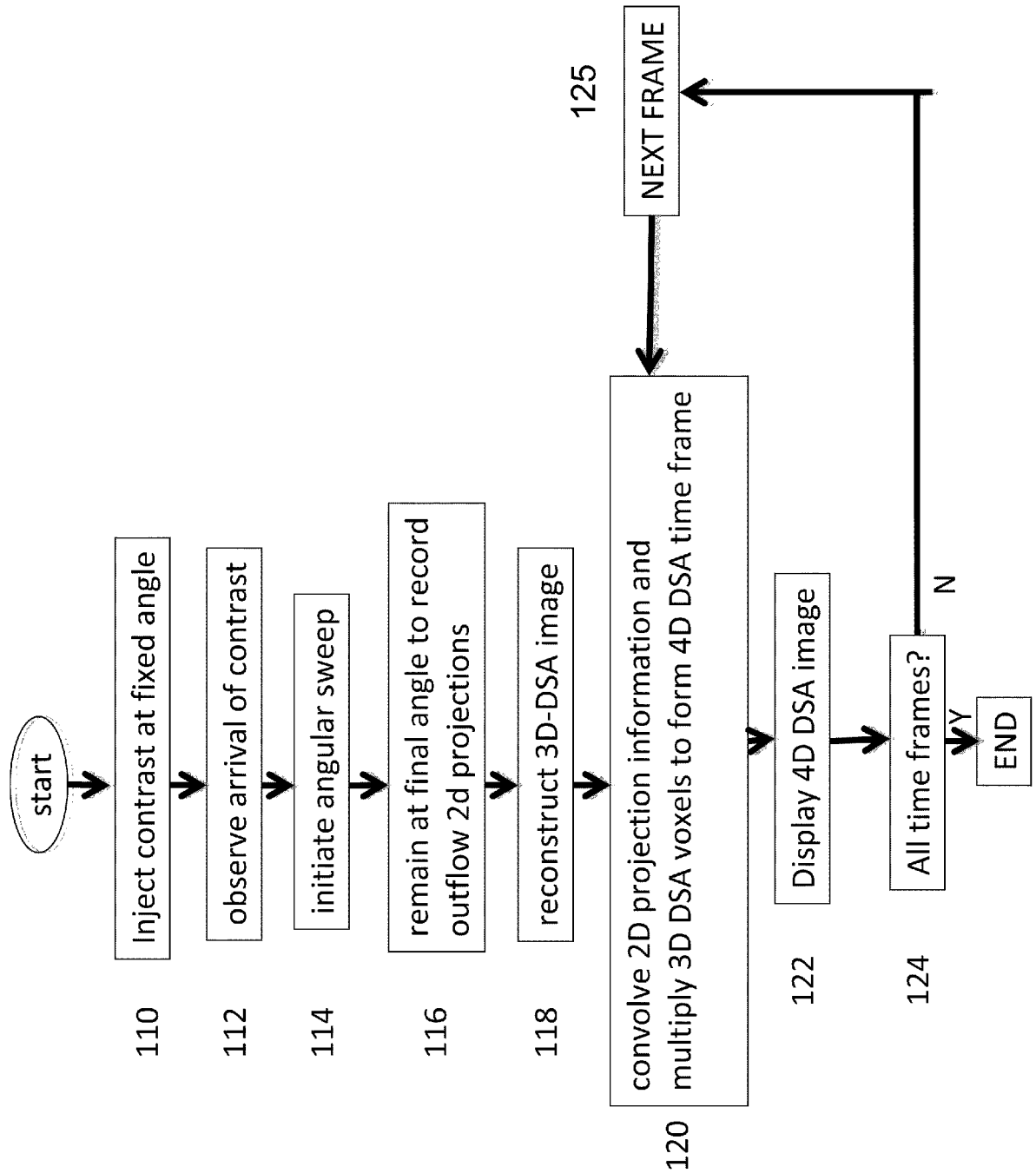
FIG. 3 is a flowchart setting forth the steps for producing a 4D-DSA image from the time-resolved 2D projection images acquired to produce a non-time-resolved 3D volume using a single plane x-ray system in accordance with the present invention.

FIG. 3 shows the acquisition method that permits the complete time dependence and 3D-DSA or CTA information to be recorded with a single injection. At process block 110 the gantry angle is fixed and 2D fluoroscopic images are taken until the arrival of contrast is observed as indicated at process block 112 and the opacification of vessels is sufficiently uniform to permit the acquisition of the rotational data set as indicated at process block 114. Following the acquisition of the rotational data, the gantry angle is held fixed and additional projections are acquired until the contrast has washed out of the vessels as indicated at process block 116. The 3D volume is then reconstructed as indicated at process block 118. The projection data are 2D-DSA images that are formed by subtracting post-contrast from pre-contrast projections at each angle. These are free from non-vascular signals. The subtracted projections are convolved and multiplied into the 3D data set to form a 4D-DSA time frame as indicated at process block 120 which is immediately displayed at a preselected projection angle using a maximum intensity projection (MIP) algorithm as indicated at process block 122. At decision block 124, if some of the frames have yet to be processed, the process moves to the next frame of the time-series of 2D-DSA images at process block 125 and repeats the selective combination process 120. This cycle continues until, at decision block 124, it is determined that a 4D-DSA image has been generated for all relevant time frames.

Figure 4:
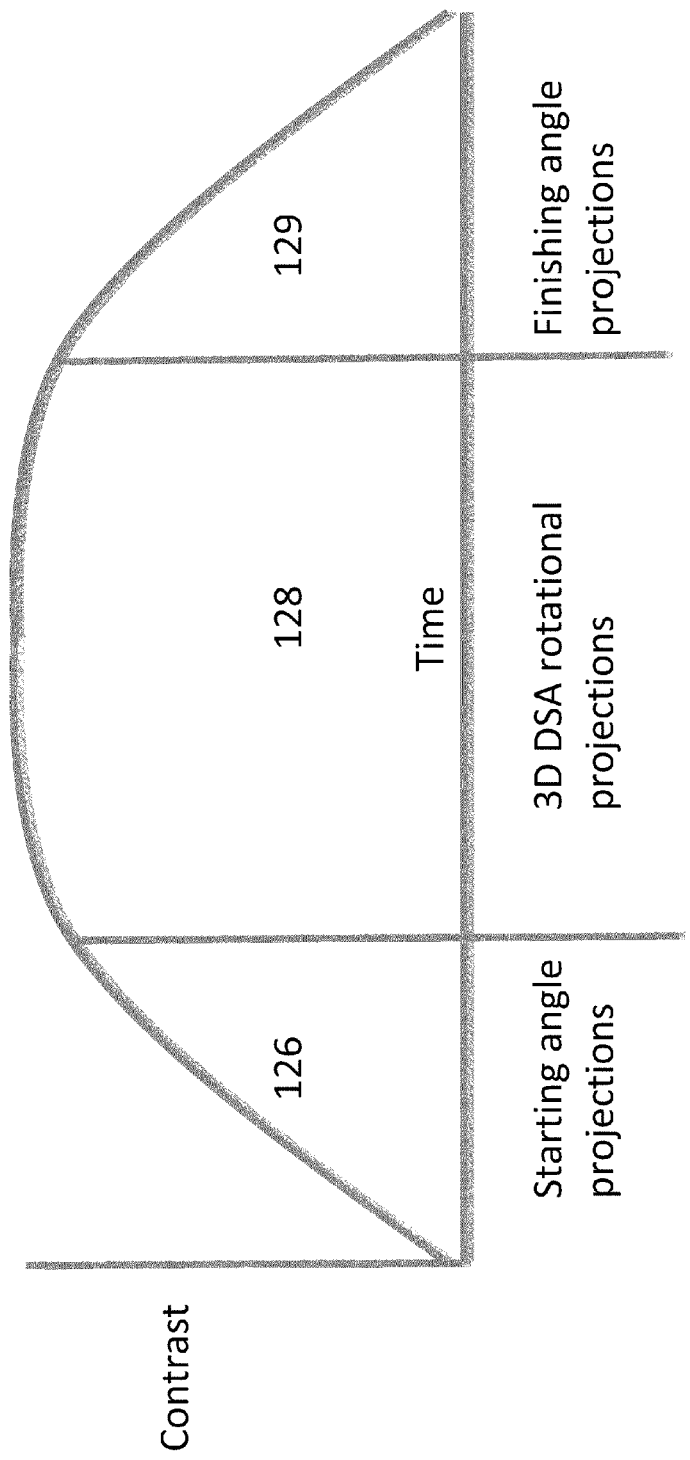
FIG. 4 shows the timing of the injected contrast arrival relative to the initiation of the rotation of the C-arm system in accordance with the present invention.

FIG. 4 illustrates the timing of the data acquisition. Following contrast injection, the arterial vessel opacification is detected in region 126 and projection images are acquired at a fixed gantry angle. When the vessel opacification has become sufficiently uniform to support a rotational DSA acquisition the gantry angle is swept and projections are acquired over a typical angular range of 200 degrees in region 128. When the gantry sweep has been completed, additional projections are acquired to depict the washout of the contrast in region 129. All acquired 2D projection data are used to produce ongoing 4D-DSA time frame volumes.

Figure 5:
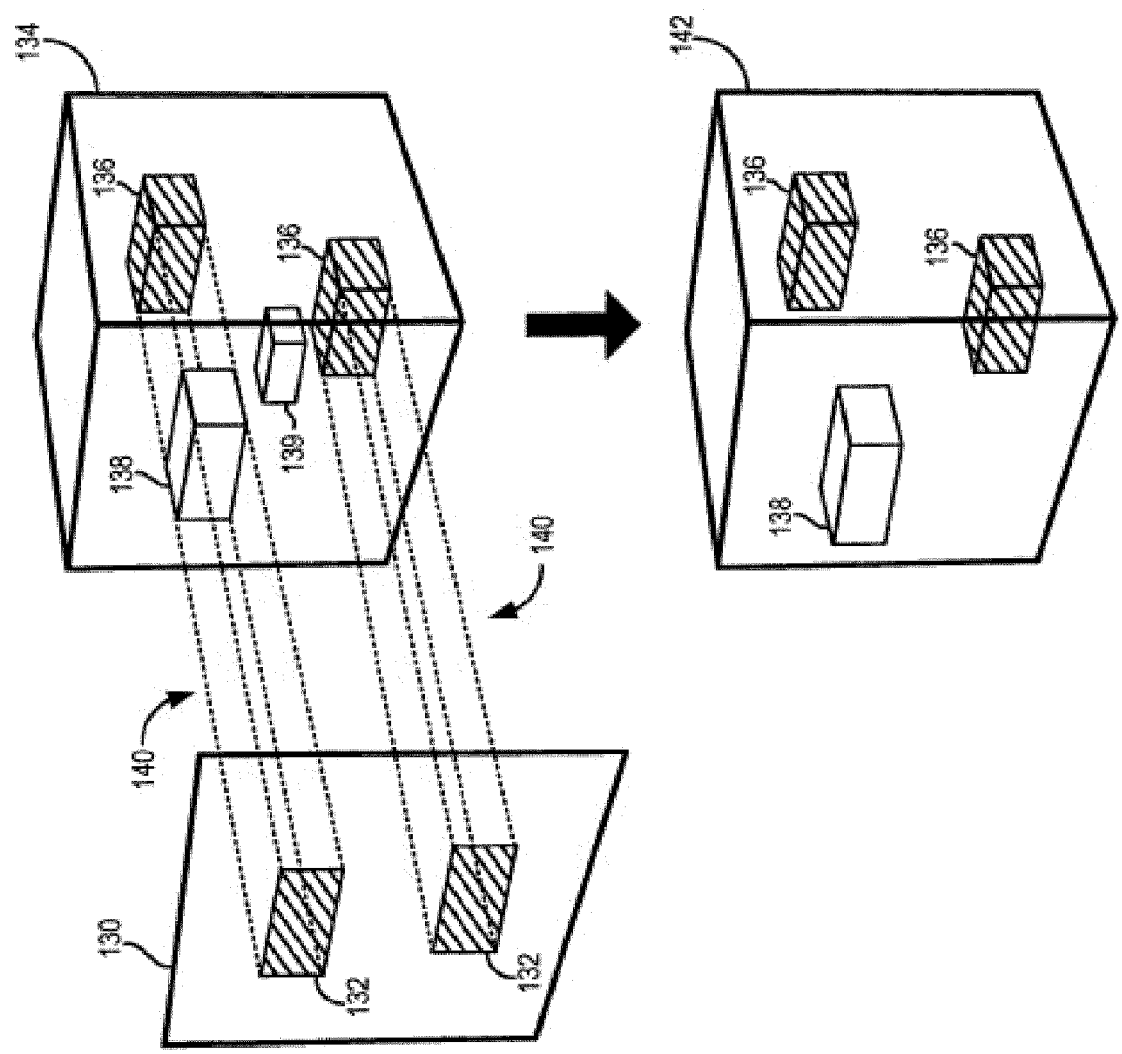
FIG. 5 schematically depicts the selective combination of a 3D image with a 2D-DSA image frame acquired using a single plane x-ray system in accordance with the present invention.

Referring now to both FIGS. 3 and 5, the images produced thus far now can be selectively combined with the steps indicated generally at 118-120 to produce a 4D-DSA image with the detailed 3D resolution of the 3D-DSA image and the temporal resolution of the time-series 2D-DSA images. In the exemplary depiction of the selective combination process provided in FIG. 5, a single frame of the time-series of 2D-DSA images 130 includes two image regions having arterial signal 132, while the 3D-DSA image 134 includes both arterial signal 136 and venous signals 138 and 139. At process block 120, a frame of the 2D-DSA image is registered to the 3D-DSA image at the selected angle and the values of the pixels in the 2D-DSA frame are projected along a line passing through each respective pixel in a direction perpendicular to the plane of the 2D-DSA frame. The projection of pixels with arterial signal 132 into the 3D-DSA image is indicated generally at 140. For simplicity, the projection of pixels in the 2D-DSA frame with no contrast is not shown. At process block 120, the 3D-DSA image 118 is weighted by the values projected from the 2D-DSA frame to produce the 4D-DSA image 122. Typically, this includes multiplying the projected values with the voxels of the 3D image that they intersect. The weighting process results in the preservation of the arterial signal 136 and the exclusion, or "zeroing-out," of undesired venous signal 139 in the 4D-DSA image 142. In addition, the intensity value of the arterial signal 132 in the 2D-DSA frame is imparted into the 3D arterial signal volume 136, thereby allowing the changes in arterial signal over time captured by the 2D-DSA images to be characterized in the 4D-DSA image 142.

The venous signal 138 preserved in the 4D-DSA image 142 illustrates a potential problem when generating 4D images using only a single time-series of 2D images acquired at a single angle. A signal from a desired structure, such as the arterial signal 132, can inadvertently be deposited in 3D voxels representing undesired structures, such as the venous region 138. The unwanted structures thus can be preserved in the 4D image as "shadow artifacts" when their signals lie along the projected values of a desired structure in a dimension inadequately characterized by the time-series of 2D images. This can result, for example, in a 4D-DSA image in which desired arterial structures are obscured by undesired venous structures for some time frames. However, this will cause a temporary anomaly in the contrast vs. time course for the vein. If the time frames of the 4D-DSA image are analyzed, this anomaly can be recognized as inconsistent with the general waveform of the vein, whereby the vein can be suppressed in the time frame where the projected arterial signal is strong. Accordingly, temporal parameters such as mean transit time (MTT) or time-to-fractional-peak can be calculated for each voxel and this information can be used to clean up shadow artifacts. To assist an operator in identifying shadow artifacts and temporal irregularities, the temporal parameters can be color-coded and superimposed on the 4D-DSA image displayed at process block 122. The temporal parameters also can be exploited to infer information related to potential diffusion abnormalities in the absence of direct perfusion information from parenchymal signals.

Figure 6:
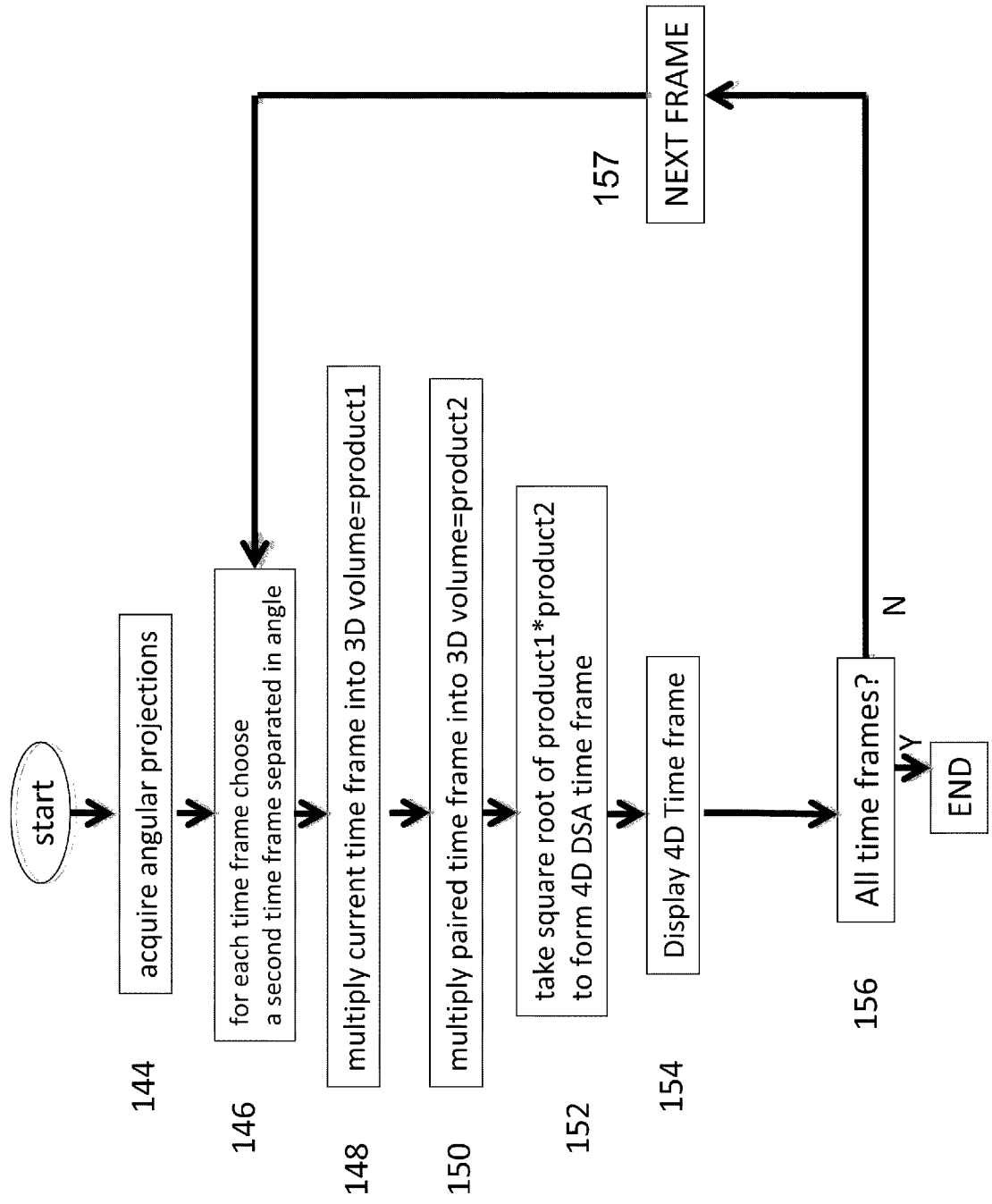
FIG. 6 is a flowchart setting forth the steps for producing a 4D-DSA image from a pair of time-resolved 2D images acquired using temporally and angularly separated intrinsic projections in accordance with the present invention.

Referring to FIG. 6, a method for producing 4D-DSA images that are less prone to shadow artifacts begins at process block 144 with the acquisition of image data at a first angle and data acquired at a second angle 146, which is typically separated from the first angle by 60 degrees. This data is preferably acquired as part of the same data set used to form the 3D-DSA volume as illustrated in FIG. 4 but could be acquired from a 2D-DSA image series acquired using a separate injection. At process block 148, the 2D data acquired at the first angle is convolved and multiplied by the 3D-DSA data to form product1. At process block 150, the second angular projection is convolved and multiplied by the 3D-DSA data set to form product2. At process block 152, the square root of the multiplication of product1 and product2 is carried out to form the current 4D-DSA time frame which is displayed at process block 154. At decision block 156, there is a check to see if all frames have been reconstructed. If some of the frames have yet to be processed, the process moves to the next frame at process block 157 and additional frames are reconstructed at process block 146.

As the first angle is advanced, the paired angle is preferably maintained at an angular separation of about 60 degrees. As the first angle increases, the available angular separation of the second and first angle is reduced gradually as the first angle gets within 60 degrees of the final angle acquired in the rotational sweep. Eventually, for the last time frames, the angular separation reduces to zero and the added benefit of the two-angle reduction of shadow artifacts gradually reduces. However, this typically occurs long after the most interesting filing dynamics of the arterial phase have been observed.

Figure 7:
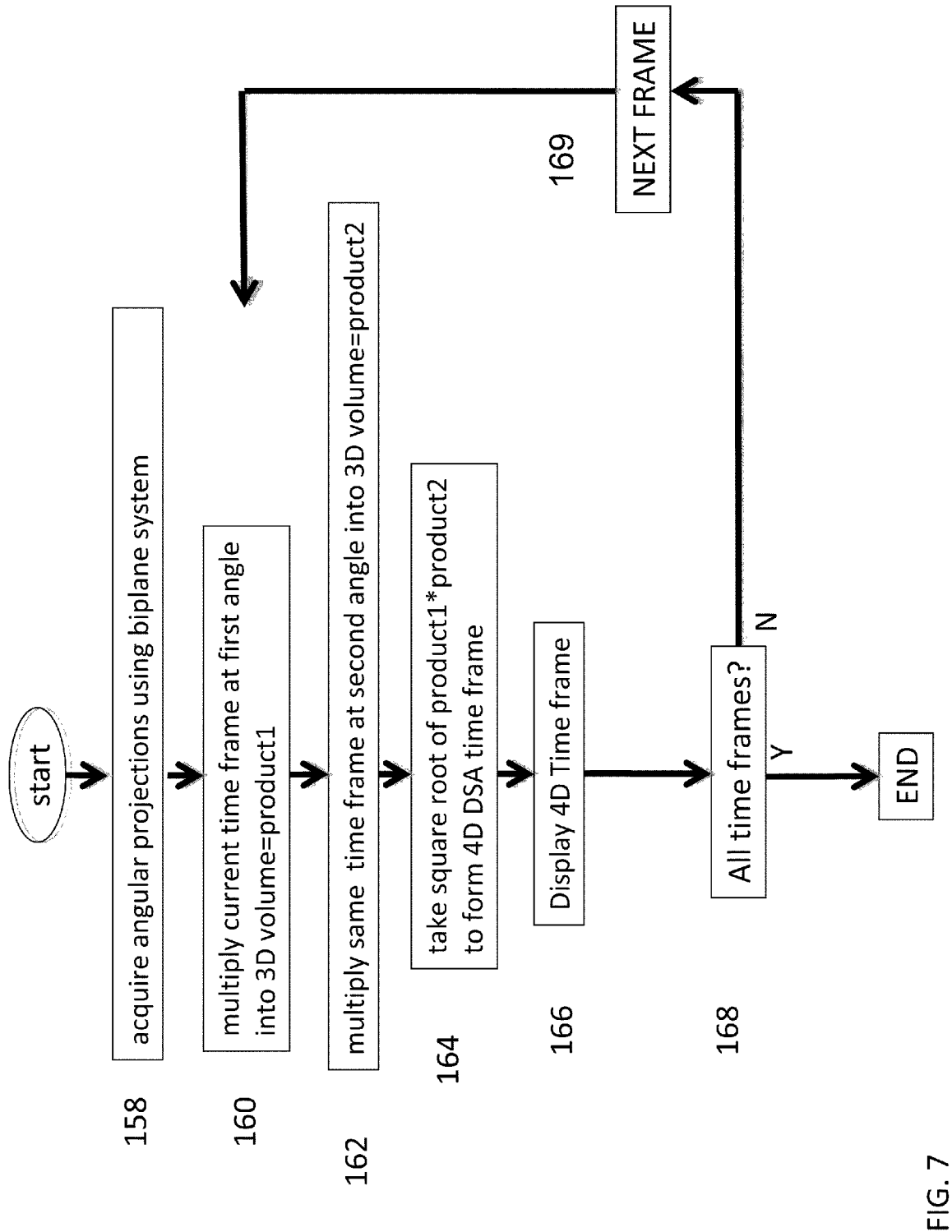
FIG. 7 is a flowchart setting forth the steps for the selective combination of a 3D image with two orthogonal 2D-DSA image frames acquired using a biplane x-ray system in accordance with the present invention.

Referring now to FIG. 7, when a bi-plane system is used, the angular separation between the projection images used to resolve the shadow artifact can be maintained. The angular projections are preferably obtained with a system in which two source detector pairs are employed to acquire rotational data. In this case, the projections used to embed the time dependence in the 3D rotational data set occur at the same point in time and are always separated by 90 degrees. Alternatively, bi-plane acquisition still can be advantageous if just one source detector pair is used for the 3D rotational acquisition and a separate injection is used to generate orthogonal 2D projections which then can be used to multiply the 3D data set.

In FIG. 7, angular projections are acquired at process block 158. The data acquired for the current time frame at the smallest angle is convolved and multiplied into the 3D data set to form product1 at process block 160. The data acquired for the current time frame at the larger angle is convolved and multiplied into the 3D data set to form product2 at process block 162. At process block 164, the square root of the product of product1 and product2 is formed to generate the current 4D-DSA time frame. This is displayed at processing block 166. At decision block 168 a check to see if all frames have been reconstructed is carried out. If some of the frames have yet to be processed, the process moves to the next frame at process block 169 and additional frames are reconstructed at process block 160. In the bi-plane implementation, the advantages of large angular separation are maintained for all time frames.

Figure 8:
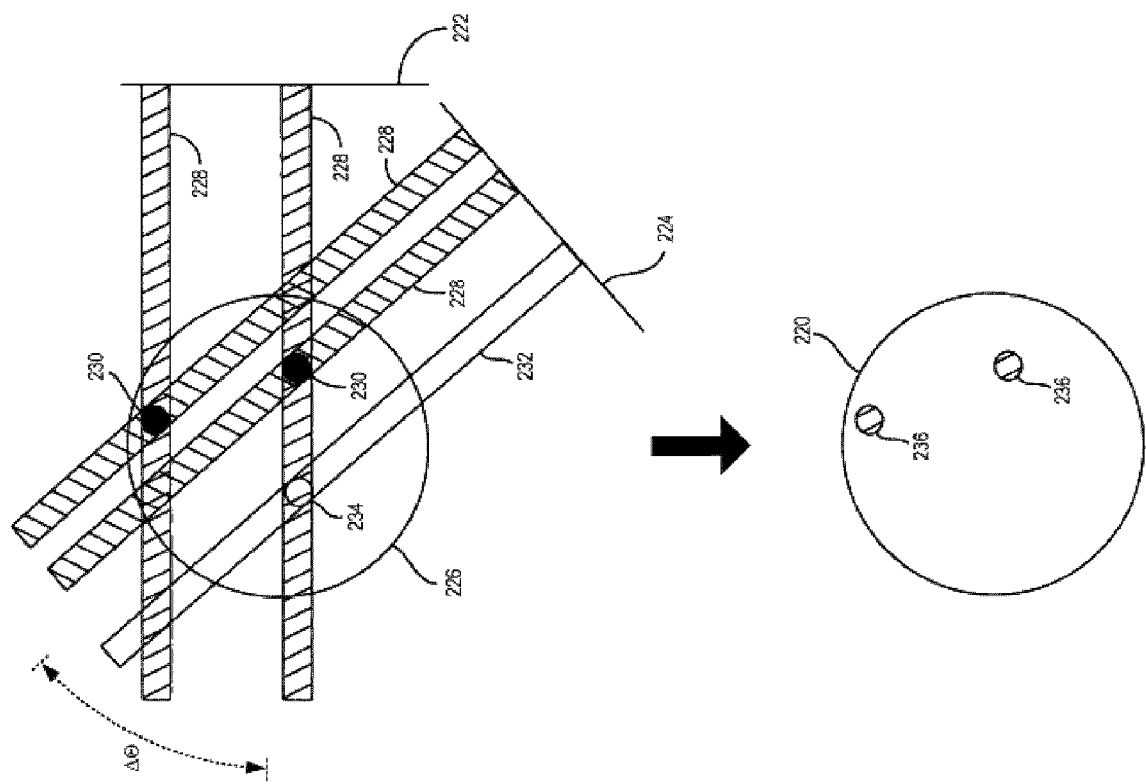
FIG. 8 schematically depicts the selective combination of a 3D image reconstructed from a full set of projection views with images generated from a pair of individual projection views selected from the set in accordance with the present invention.

FIG. 8 illustrates the use of two angles to remove shadow artifacts. Schematically shown is the formation of a 4D-DSA image frame 220 by selectively combining two registered projection images 222 and 224 and a 3D-DSA image without time dependence 226. Projected arterial signal 228 from the projection images 222 and 224 weights arterial voxels 230 in the 3D-DSA image 226, while the projected signal from pixels without contrast 232 nullifies venous voxels 234 in the 3D-DSA image 226. The resulting 4D-DSA image frame 220, thus, includes weighted arterial signal 236, but does not include undesired venous signals, despite the fact the venous voxels 234 and arterial voxels 230 of the 3D-DSA image are aligned for one of the projection images.

Figure 9:
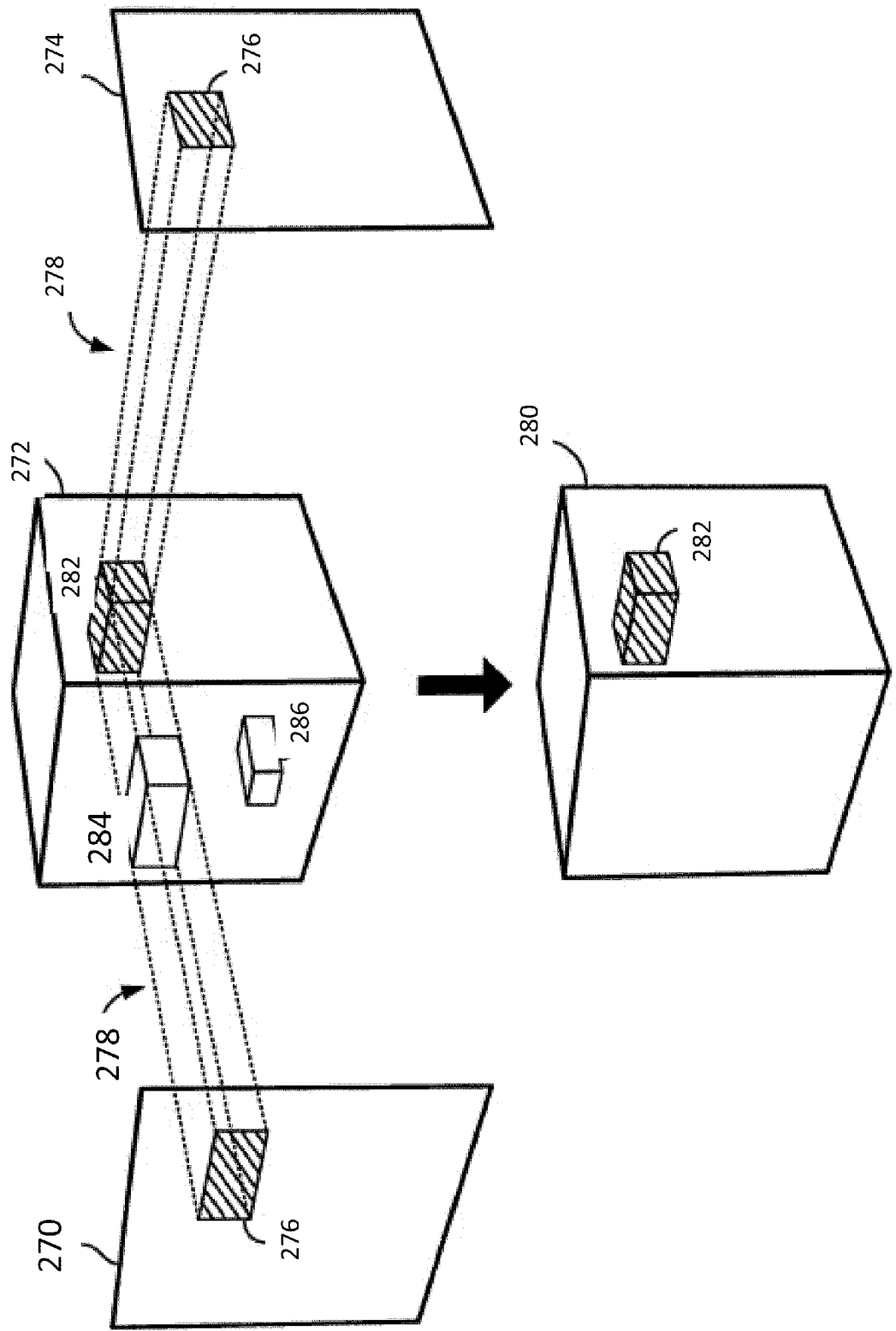
FIG. 9 schematically depicts the multiplication process involving the combination of 2D projection information from two orthogonal angles as produced from a bi-plane system and the 3D DSA volume.

In FIG. 9, this process is illustrated for the case of bi-plane acquisition. The projection of arterial signal 276, that is, pixels having contrast, is indicated generally at 278. The projected values from both of the orthogonal 2D-DSA frames are used to weight the 3D-DSA image and thus produce the 4D-DSA frame 280. Venous signals 284 and 286 are zeroed-out by virtue of being absent in either of the 2D projection images 270 or 274, registered to the 3D-DSA image 272, resulting in the unambiguous isolation of the arterial signal in 282. Again, both the 3D-DSA and orthogonal 2D-DSA images are acquired while a contrast agent is administered to the subject and a signal corresponding to non-vascular structures is removed by subtracting out a mask image.

Time-resolved 3D images produced in accordance with the present invention have significantly improved spatial and temporal resolution over images produced using traditional methods and, thus, have great utility in the diagnosis, pretreatment planning, and post-treatment assessment of complex vascular conditions. In addition, these images allow the implementation of time-resolved true 3D roadmaps for use in minimally invasive interventional procedures, thereby facilitating the improved manipulation of surgical devices in complex vasculature. In particular, the present invention allows the implementation of 4D fluoroscopy using real-time sequences of surgical device movement combined with spatially and temporally selectable roadmaps obtained from 4D-DSA images. For example, catheter information acquired via either single plane or biplane fluoroscopy can be embedded within 4D-DSA vascular time frames to permit viewing at an arbitrary angle without further gantry movement. Catheter information acquired via real-time single projection subtracted fluoroscopy likewise can be superimposed on 4D-DSA time frames that are registered as the gantry angle is adjusted.

Figure 10:
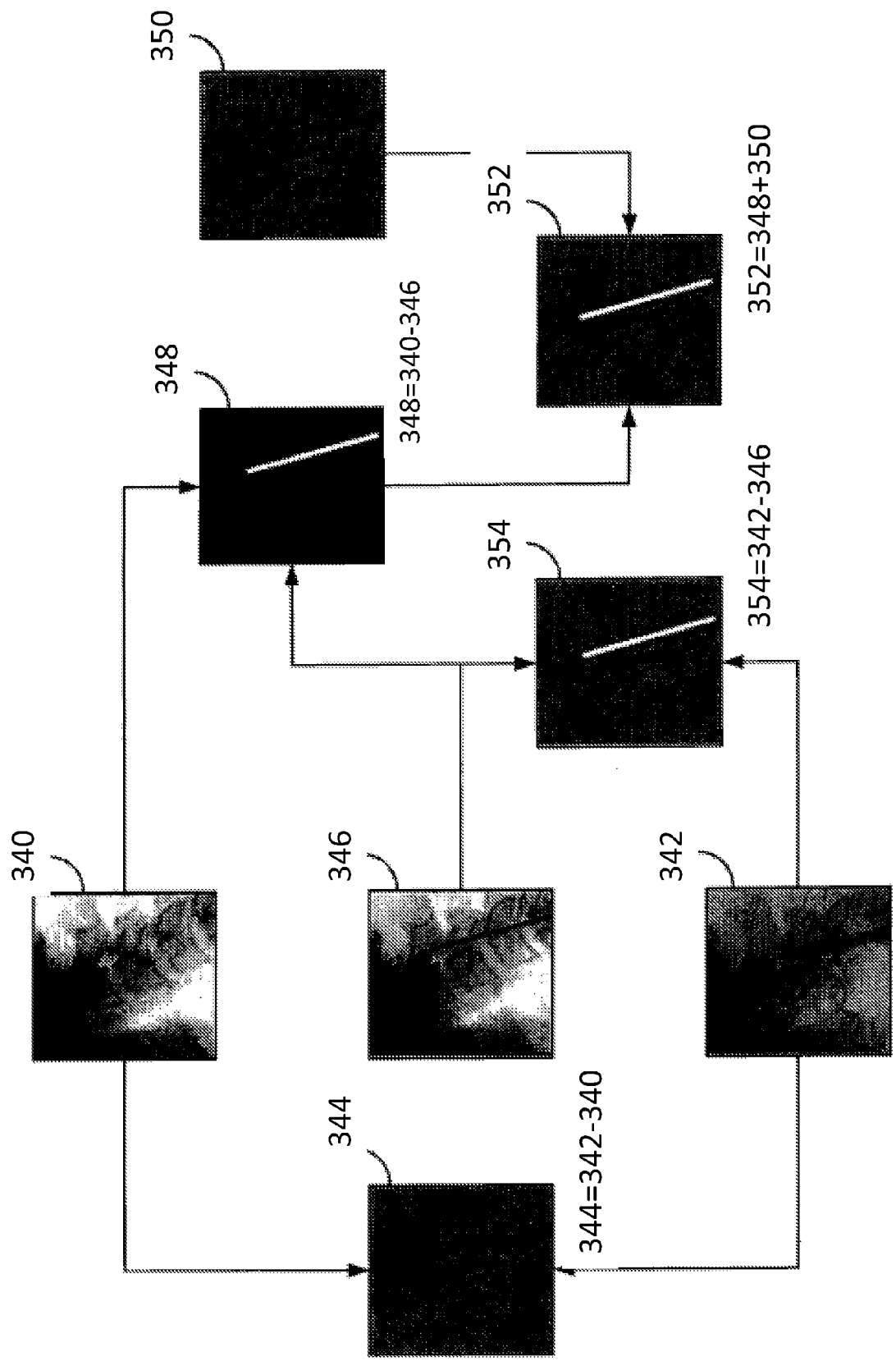
FIG. 10 depicts the combination of images involved in generating a 4D fluoroscopic image, the images being temporally differentiated and used to form correlated segments of the advancing interventional device as in FIG. 11.

Referring to FIG. 10, in the formation of a fluoroscopic image, it is important that the spatial resolution of the surgical device be maintained. This can differ from the formation of 4D-DSA time frames where time-resolved 2D-DSA time frames are convolved and used to get a local spatial estimate of temporal weighting. It is better to provide an unconvolved and isolated depiction of the surgical device information so that resolution is maintained, though it should be noted that the lack of convolution requires more precise image registration. The formation of images suitable for proper magnification and registration between a moving surgical device, a catheter, and a 4D-DSA image frame is illustrated in FIG. 10. With the catheter mostly out of the field-of-view (FOV), fluoroscopic images 340 and 342 are obtained before and after contrast injection, respectively. These images are subtracted to define an image 344 of the vessel position in the fluoroscopic image series. The catheter is then advanced to obtain image 346, which is subtracted from 340 to form the catheter-only image 348 that is added to a selected 4D-DSA frame 350 to form the 4D fluoroscopic image 352. For comparison, in traditional fluoroscopy, a fluoroscopic image 354 is formed by subtracting the image 346 depicting the advanced catheter from the fluoroscopic image 342 obtained after contrast injection.

When embedding surgical device information acquired via biplane fluoroscopy in 4D-DSA images, the fluoroscopic images are acquired in orthogonal pairs and the above process can be performed for both images. In this case, objects in the resulting 4D fluoroscopic image 352 are registered with the single projection bi-plane images 340-346. Generally, the first step in the registration process is the application of block matching with variable magnification and position in order to register images 344 and 350 in lateral and coronal views. Then the catheter image 348 is added in to form the 4D fluoroscopic image 352, which is registered to the traditional fluoroscopic image 354 using block matching. A range of horizontal and vertical magnifications are typically searched during the registration procedure. For each magnification, a spatially displaced block search can be used to minimize the sum of absolute differences between 4D-DSA time frames and displaced fluoroscopic time frames, and the magnification and translation that minimizes this sum may be chosen for registering the images. To accelerate the search procedure in fluoroscopic dose reduction algorithms, it is possible to employ an iterative block matching technique that initially uses large blocks and then proceeds to smaller blocks.

The formation of a catheter image, such as image 348, can be noisy due to the multiplicative combination of noise from two biplane time-resolved images. Therefore, a noise reduction scheme may be implemented prior to the combination of the catheter image and the 4D-DSA time frame. For example, a spatially adaptive linear filter may be used so that in each element of an image sub-region matrix, the direction of the catheter is determined by calculating the sum of the pixel value within the block as a test object similar in size to the catheter is rotated through the block. The minimal sum is, thus, achieved when the test object has the same orientation as the catheter and a linear convolution filter can be applied along this direction to reduce catheter discontinuities caused by noise in acquired biplane images. Different grid sizes, test object rotation angles, and translation scheduling can be used depending on image quality and processing speed requirements. The size of the linear convolution kernel also can be varied to achieve a desired balance between noise and discontinuity reduction and potential errors in catheter tip localization. Following the application of this spatially adaptive linear filter, a motion adaptive integration of fluoroscopic image frames also can be used to reduce noise. Alternative spatially adaptive filters also may be used to improve the intelligibility of catheter images. For example, another approach is to scan the initial catheter images point-by-point and look at the direction in which the maximum linear sum over some number of pixels occurs. The linear filter then may operate in this direction, since it corresponds to the local orientation of the catheter. Depending on the size of the convolution kernel, the search grid can be adjusted and multiple convolutions of the same catheter segment may be performed.

A distinction should be considered when comparing the relative noise properties of the fluoroscopic and DSA applications. In the case of generating 4D-DSA frames, the anatomical details are supplied by the 3D-image, for example, as acquired by a rotational DSA examination, and the acquisition's individual projections or independently acquired 2D-DSA images provide a local spatially averaged estimate of how much the vasculature is present at each point in time. This spatial average reduces noise and it is not required that the spatial information of the time-dependent frames be maintained. In contrast, it is beneficial to maintain the spatial resolution of the fluoroscopic images depicting the catheter so that there is no intrinsic noise averaging except for that imposed by the filters discussed above. It also should be noted that the computation time for generating 4D-DSA frames and generating 4D fluoroscopic images can differ significantly. It is not necessary to reconstruct 4D-DSA images in real time, whereas fluoroscopic images should be subjected to registration and noise averaging algorithms in real time with minimal latency.

With a biplane fluoroscopy system, surgical device information from an orthogonal time-resolved image series is typically multiplied into a binarized version of the 3D rotational DSA voxels. Following projection from one dimension there is uniform deposition of a surgical device signal across the vasculature depicted in the 3D rotational DSA voxels. The intersection of this signal with a corresponding signal from the orthogonal view carves out the 3D catheter voxels. A single plane system cannot acquire this additional orthogonal view. However, an alternative is to deposit all of the catheter signal in the center of the vessels depicted in a binary rotational DSA display. The maximum intensity projection (MIP) through this data set at any point in time then can be superimposed on the MIP through a corresponding 4D-DSA time frame, thus resulting in images that are roughly equivalent to those produced using biplane methods with the advancement of the surgical device being well represented. This approach of constraining the catheter to the center of a vessel in the direction not captured by the single plane acquisition does not involve any significant disadvantage compared to traditional fluoroscopic views in which catheter position is unknown in one direction.

For systems without biplane capabilities, the flexibility of roadmap selection provided by the 4D-DSA time frames additionally can be exploited by superimposing the single plane fluoroscopy on the MIP of the 4D-DSA time frame taken at a given gantry angle. This involves registration at just the current projection for each gantry angle. Because it is not necessary that orthogonal surgical device views intersect to form a 3D spatial catheter volume, registration is of less importance and the full image quality of live fluoroscopy is essentially maintained. It is contemplated that this gantry rotation mode offers improved SNR, since it does not involve the multiplicative noise effects that occur when embedding biplane surgical device information into a 4D-DSA image, as discussed above, to establish a 4D fluoroscopic volume without gantry rotation.

Figure 11:
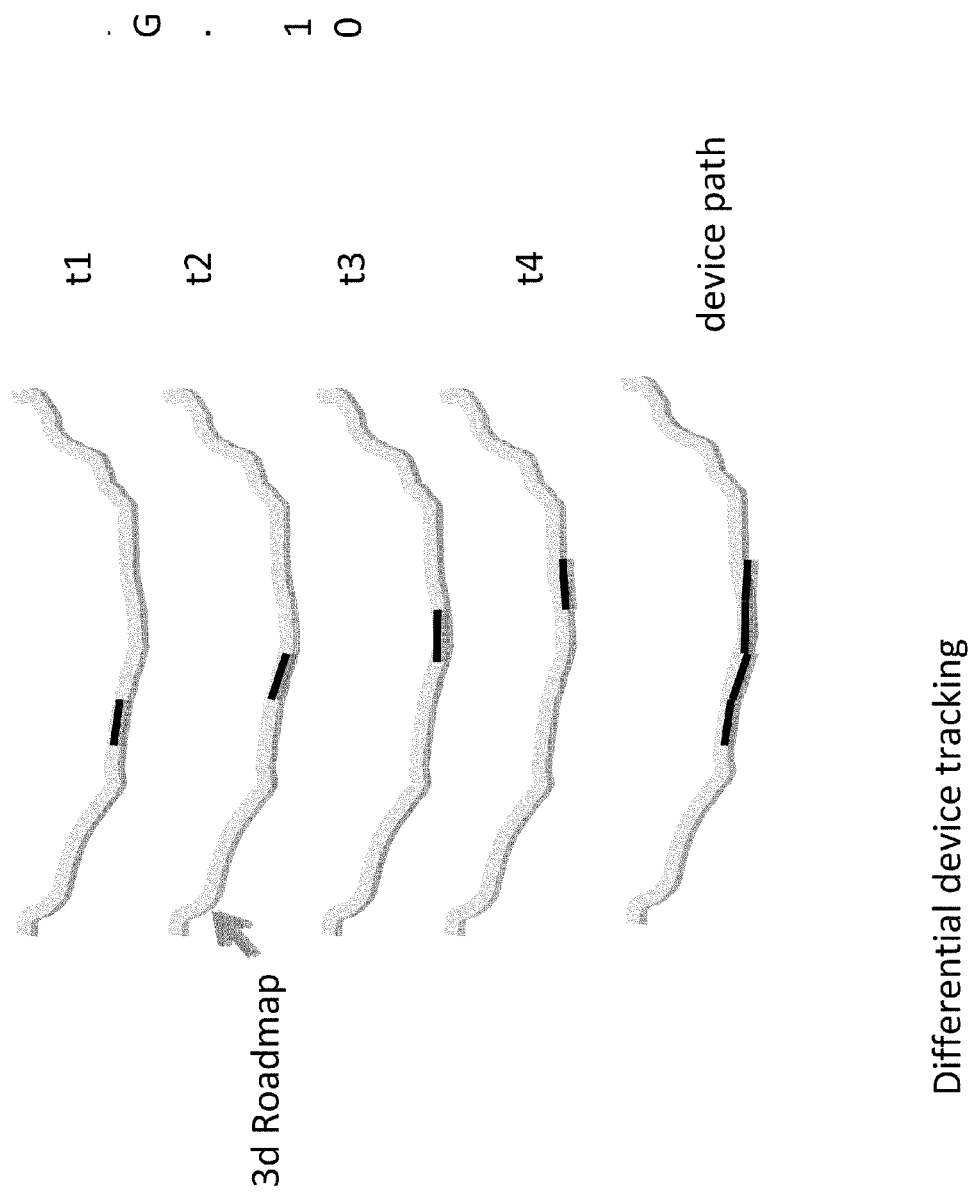
FIG. 11 shows the fluoroscopic images generated in accordance with FIG. 10 which are temporally subtracted with a time separation of at least one frame to generate time segments indicating the most recent change in the device tip, whereby after multiplication of these segments into the 3D volume from two projection angles the correlated segments are summed to produce a device path.

For fluoroscopic applications in which there are likely to be multiple positions of the interventional device within the vascular lumen, ambiguous intersections of current information and information associated with the past history of the device trajectory can arise. Because of this, the fluoroscopic image series generated at 352 in FIG. 10 are sequentially subtracted using a frame separation of at least one in order to isolate the most recent change in device position. The differential signals in the biplane views are well-correlated in time and, when multiplied by the 3D data set, reliably isolate the current position of the tip of the device. This is illustrated in FIG. 11 where the current device tip is shown at times t1-t4. A display of the device path is formed by summing the past catheter position signals using a simple sum or a recursive filter. This display can be reset by the operator to reinitiate integration.

Figure 12:
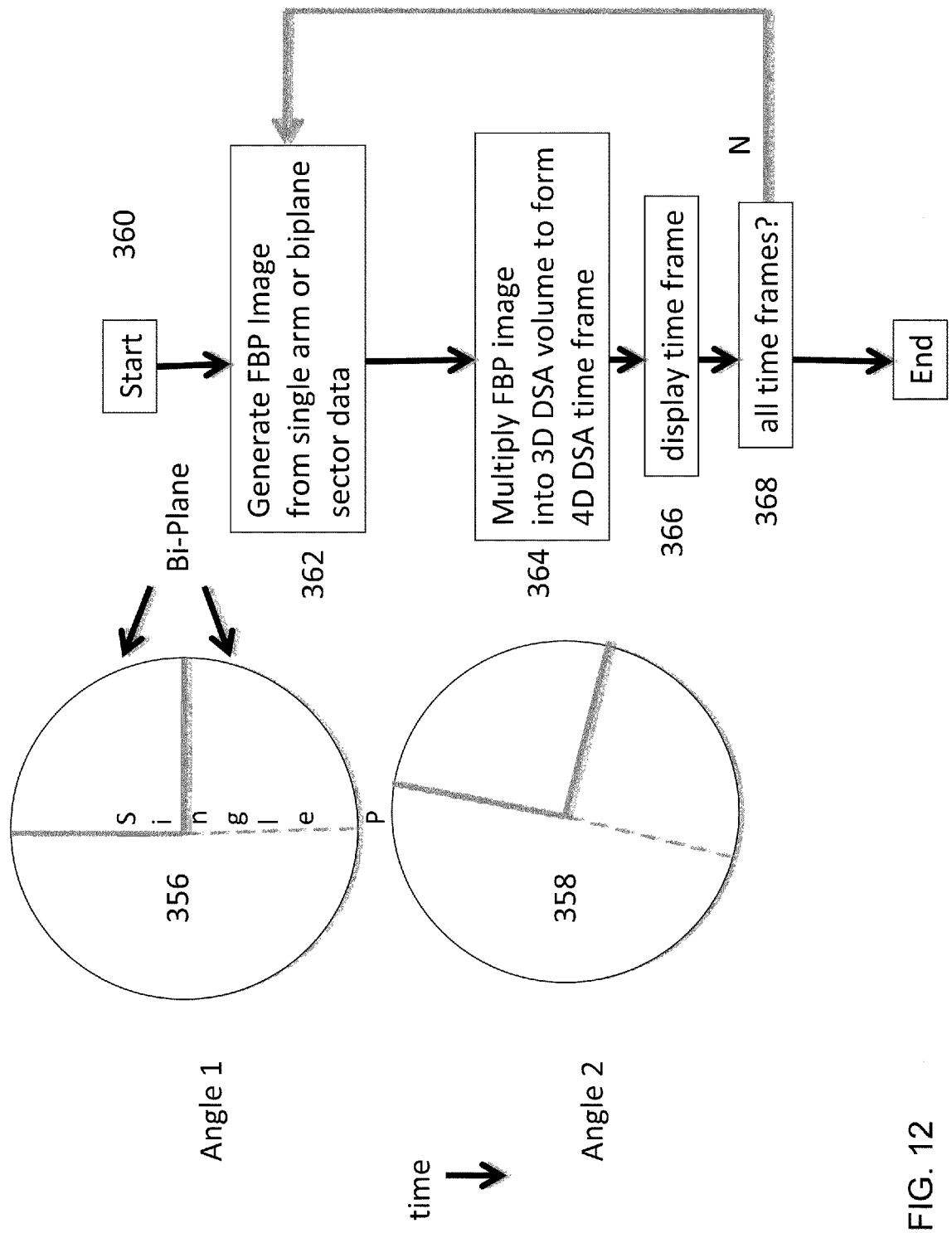
FIG. 12 shows a schematic and flow chart depicting the limited angle filtered back projection method whereby either one or two angular sectors are acquired depending on whether a single plane or bi-plane system is used.

FIG. 12 illustrates the method for employing partial angle filtered back projection (FBP) images to weight the information in the 3D-DAS volume to form 4D-DSA time frames. Partial angle sector data are acquired as a function of time as shown in 356 and 358. The angular sectors are advanced as time goes on. For a single plane system, a single sector of projection angles are acquired for each time frame. For a system employing two source detector sets, the number of sectors is increased to two resulting in an improved reconstruction. In a flowchart 360 of the method, the FBP image is formed at process block 362 and used to weight the 3D volume data at process block 364 to form a 4D-DSA time frame that is displayed at process block 366. At decision block 368, a decision is made regarding the need to reconstruct new frames in which case the process returns to 362.

Figure 13:
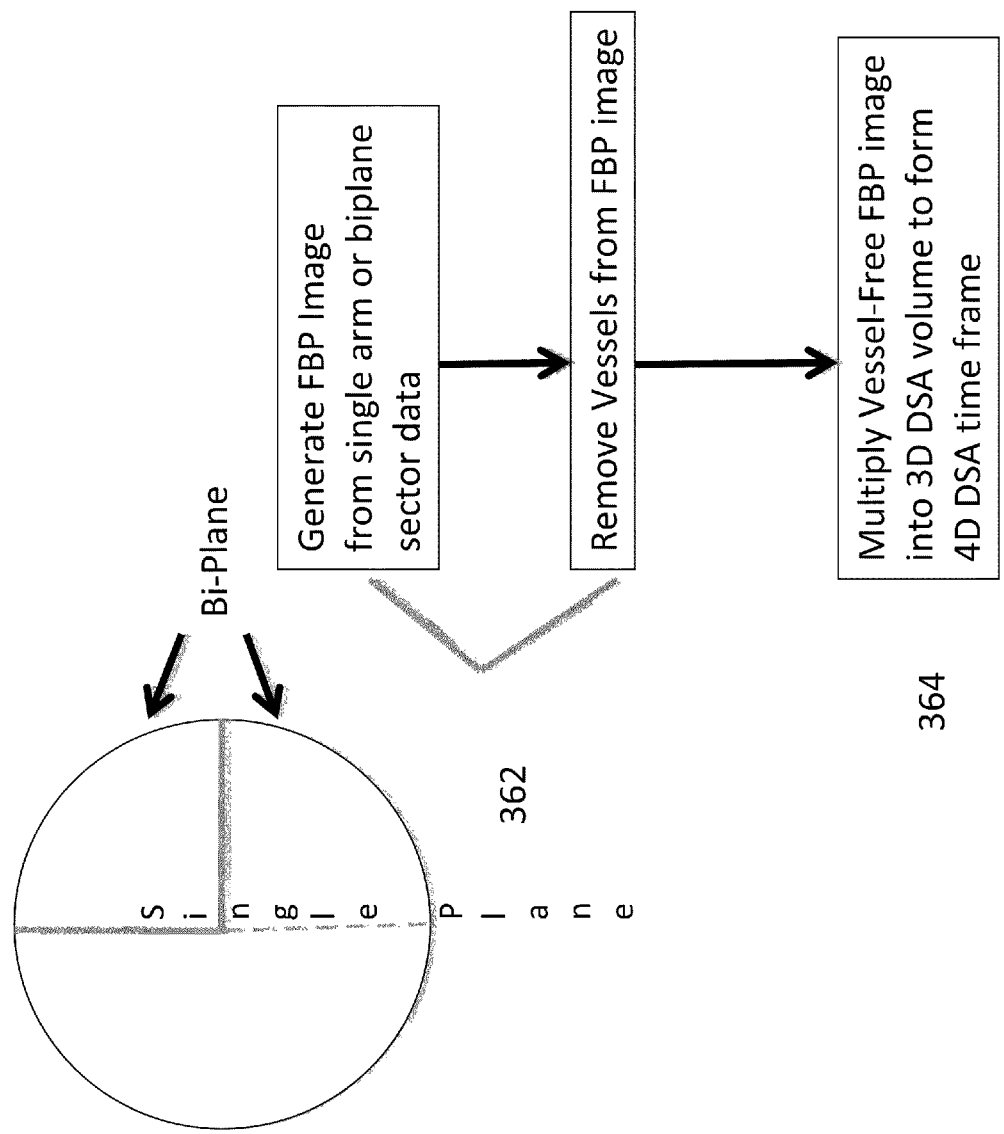
FIG. 13 shows a schematic and flow chart depicting the selective elimination of vascular information in the limited angle reconstruction prior to multiplication which increases sensitivity to the tissue perfusion and reduces reconstruction errors from the more dominant vascular signals.

When it is desired to generate time-dependent 3D volumes depicting tissue perfusion it is desirable to remove vascular information from the weighting image. This can be done by applying a threshold eliminating signal above a user-defined level. This step can be incorporated into an "expanded" processing step 362 prior to weighting the 3D volume in processing block 364 as shown in FIG. 13. This process diminishes the effects of errors in the reconstruction of the vessels that might compete with the tissue perfusion signals.

Although the present invention has been described with reference to specific embodiments, those of skill in the art will recognize that changes may be made thereto without departing from the spirit and scope of the present invention as set forth in the hereafter appended claims.

The invention claimed is:

1. A method for producing a time-resolved three-dimensional image of a subject, the method comprising:
   acquiring image projection data from the subject using a medical imaging system during a single contrast injection, the medical imaging system including a single source/single detector system;
   generating a time-series of two-dimensional images from at least a portion of the acquired image projection data;
   reconstructing a three-dimensional image substantially without temporal resolution from at least a portion of the acquired image projection data;
   selecting, for each two-dimensional image in the time-series, a current image and a paired image;
   multiplying, for each two-dimensional image in the time-series, the current image into the three-dimensional image substantially without temporal resolution to determine a first product value;

multiplying, for each two-dimensional image in the time-series, the paired image into the three-dimensional image substantially without temporal resolution to determine a second product value;

taking the square root of the multiplication of the first and second product values to produce a frame of a time-resolved three-dimensional image having a signal-to-noise ratio substantially higher than a signal-noise-ratio of the acquired image projection data, wherein one or more voxels in the frame is nullified based on the current image or the paired image; and combining frames of the time-resolved three-dimensional image to form the time-resolved three-dimensional image.

2. A method as claimed in claim 1, wherein a subtracted vessel-only time-series of two-dimensional images is generated by subtracting at least one of a time frame of the time-series and an average of time frames of the time-series acquired before arrival of contrast from frames of the time-series acquired after an arrival of contrast during the single contrast injection.

3. A method as claimed in claim 1, wherein the one or more nullified voxels in the frame of the time-resolved three-dimensional image correspond to undesired vascular structures.

4. A method as claimed in claim 1, wherein each two-dimensional image in the time-series correspond to images acquired at different angles.

5. A method as claimed in claim 1, further comprising determining a temporal parameter for each voxel of the time-resolved three-dimensional image, wherein the temporal parameter is at least one of a mean transit time and time-to-fractional peak.

6. A method as claimed in 5, wherein determining a temporal parameter includes removing shadowing artifacts from the time-resolved three-dimensional image based on the temporal parameter.

7. A method as claimed in claim 5, wherein determining a temporal parameter includes superimposing a color coded display of the temporal parameter on at least one of the time-resolved three-dimensional image and a blood volume image generated from the three-dimensional image substantially without temporal resolution.

8. A method as claimed in claim 1, wherein the image projection data are acquired at a fixed position of a source detector gantry of the single source/single detector system until injected contrast is detected in a field of view and generates adequate arterial and venous contrast to permit acquisition of a three-dimensional rotational data set with substantially uniform contrast throughout whereby rotation of the source detector gantry is initiated.

9. A method as claimed in claim 8, wherein additional time-resolved outflow projection data are acquired at a final angle of the three-dimensional rotational data set acquisition and are used to produce three-dimensional time resolved outflow volumes.

10. A method as claimed in claim 1, wherein the single contrast injection is one of an intra-arterial injection and an intra-venous injection.

11. A method as claimed in claim 1, further comprising applying a threshold elimination signal prior to a progressive time-series of two-dimensional images being used to weight and multiply the three-dimensional image substantially without temporal resolution to remove vascular information.

12. The method of claim 1, wherein the time-resolved three-dimensional image comprises a time series of three dimensional images, wherein each three dimensional image in the series is generated based on a combination of the three-dimensional image substantially without temporal resolution and a respective pair of two dimensional images obtained at different projection angles.

13. The method of claim 1, wherein the time-resolved three-dimensional image is fully rotatable.

14. The method of claim 13, wherein the time-resolved three-dimensional image has a resolution of at least about $512^3$ pixels and a frame rate of at least about 30 frames per second.

15. A method for producing a time-resolved three-dimensional image of a subject, the method comprising:

acquiring image projection data from the subject using a medical imaging system during multiple contrast injections acquired at multiple source-detector orientations, the medical imaging system including a single source/single detector array;

generating a subtracted vessel-only time-series of two-dimensional images from the acquired image projection data at the multiple source-detector orientations;

reconstructing a three-dimensional image substantially without temporal resolution from at least a portion of the acquired image projection data;

selecting, for each two-dimensional image in the time-series, a set of n number of images, wherein n is greater than 1, and wherein each two-dimensional image corresponds to a different time;

multiplying, for each two-dimensional image in the time-series, the images in the set of n number images into the three-dimensional image substantially without temporal resolution to determine a set of n number of product values;

taking the nth root of the set of n number of product values to produce a frame of a time-resolved three-dimensional image with a signal-to-noise ratio substantially higher than a signal-to-noise ratio of the acquired image projection data, wherein one or more voxels in the frame is nullified based on the set of n number images.

16. A method as claimed in claim 15, wherein the image projection data is acquired at multiple rotation angles during one of the multiple contrast injections.

17. A method as claimed in claim 16, wherein a three-dimensional image substantially without temporal resolution is reconstructed from at least a portion of the acquired image projection data.

18. A method as claimed in claim 15, wherein the one or more nullified voxels in the frame of the time-resolved three-dimensional image correspond to undesired vascular structures.

19. A method as claimed in claim 18, wherein each two-dimensional image in the time-series correspond to images acquired at different angles.

20. A method as claimed in claim 15, further comprising determining a temporal parameter for each voxel of the time-resolved three-dimensional image, wherein the temporal parameter is at least one of a mean transit time and time-to-fractional peak.

21. A method as claimed in claim 20, wherein determining a temporal parameter includes removing shadowing artifacts from the time-resolved three-dimensional image based on the temporal parameter.

22. A method as claimed in claim 20, wherein determining a temporal parameter includes superimposing a color coded display of the temporal parameter on at least one of the time-resolved three-dimensional image and a blood volume image generated from the three-dimensional image substantially without temporal resolution.

23. A method as claimed in claim 15, wherein the multiple contrast injections are one of intra-arterial injections and intra-venous injections.

24. A method for producing a time-resolved three-dimensional image of a subject, the method comprising:
acquiring image projection data from the subject using a medical imaging system during a single contrast injection, the medical imaging system including a bi-plane system having two separate source detector systems;
generating a subtracted vessel-only time-series of two-dimensional images from at least a portion of the acquired image projection data from each of the source detector systems obtained at multiple angles;
reconstructing a three-dimensional image substantially without temporal resolution from at least a portion of the acquired image projection data;
selecting, for each two-dimensional image in the time-series, a current image and a paired image;
multiplying, for each two-dimensional image in the time-series, the current image into the three-dimensional image substantially without temporal resolution to determine a first product value;
multiplying, for each two-dimensional image in the time-series, the paired image into the three-dimensional image substantially without temporal resolution to determine a second product value;
taking the square root of the multiplication of the first and second product values to produce a frame of a time-resolved three-dimensional image having a signal-to-noise ratio substantially higher than a signal-to-noise ratio of the acquired image projection data, wherein one or more voxels in the frame is nullified based on the current image or the paired image.

25. A method as claimed in claim 24, wherein the one or more nullified voxels in the frame of the time-resolved three-dimensional image correspond to undesired vascular structures.

26. A method as claimed in claim 24, further comprising determining a temporal parameter for each voxel of the time-resolved three-dimensional image, wherein the temporal parameter is at least one of a mean transit time and time-to-fractional peak.

27. A method as claimed in claim 26, wherein determining a temporal parameter includes removing shadowing artifacts from the time-resolved three-dimensional image based on the temporal parameter.

28. A method as claimed in claim 26, wherein determining a temporal parameter includes superimposing a color coded display of the temporal parameter on at least one of the time-resolved three-dimensional image and a blood volume image generated from the three-dimensional image substantially without temporal resolution.

29. A method as claimed in claim 24, wherein the image projection data are acquired at fixed positions of two source detector gantries of the respective two source detector systems until injected contrast is detected in a field of view and generates adequate arterial and venous contrast to permit acquisition of a 3D rotational data set with substantially uniform contrast throughout whereby rotation of at least one of the two source detector gantries is initiated.

30. A method as claimed in claim 29, wherein additional time-resolved outflow projection data are acquired at a final angle of the three-dimensional rotational data set acquisition and are used to produce three-dimensional time resolved outflow volumes.

31. A method for producing a time-resolved three-dimensional image of a subject, the method comprising:
acquiring first image projection data from the subject using a medical imaging system during a first contrast injection, the medical imaging system including a bi-plane system having two separate source detector systems;
generating a subtracted vessel-only time-series of two-dimensional images from at least a portion of the acquired first image projection data from each of the source detector systems;
acquiring second image projection data from the subject using the medical imaging system during a second contrast injection;
reconstructing a three-dimensional image substantially without temporal resolution from at least a portion of the acquired second image projection data;
selecting, for each two-dimensional image in the time-series, a current image and a paired image;
multiplying, for each two-dimensional image in the time-series, the current image into the three-dimensional image substantially without temporal resolution to determine a first product value;
multiplying, for each two-dimensional image in the time-series, the paired image into the three-dimensional image substantially without temporal resolution to determine a second product value;
taking the square root of the multiplication of the first and second product values to produce a frame of a time-resolved three-dimensional image having a signal-to-noise ratio substantially higher than a signal-to-noise ratio of the acquired first image projection data, wherein one or more voxels in the frame is nullified based on the current image or the paired image.

* * * * *